United States Patent [19]

Maryanoff

[11] Patent Number: 4,743,400
[45] Date of Patent: May 10, 1988

[54] PROCESS FOR PREPARING RETINOYL CHLORIDES

[75] Inventor: Cynthia A. Maryanoff, Solebury Township, Bucks County, Pa.

[73] Assignee: McNeilab, Inc., Ft. Washington, Pa.

[21] Appl. No.: 909,794

[22] Filed: Sep. 22, 1986

[51] Int. Cl.[4] .......................................... C07C 175/00
[52] U.S. Cl. ............................... 260/408; 260/544 L; 564/188; 564/172
[58] Field of Search ............................ 260/408, 544 L

[56] References Cited

U.S. PATENT DOCUMENTS

| | | | |
|---|---|---|---|
| 4,055,659 | 10/1977 | Gander et al. | 424/305 |
| 4,108,880 | 8/1978 | Gander et al. | 260/410.5 |
| 4,190,594 | 2/1980 | Gander et al. | 260/404 |
| 4,323,581 | 4/1982 | Gander | 424/324 |

FOREIGN PATENT DOCUMENTS

| | | |
|---|---|---|
| 2306112 | 8/1974 | Fed. Rep. of Germany . |
| 2456959 | 6/1976 | Fed. Rep. of Germany . |
| 2843870 | 4/1980 | Fed. Rep. of Germany . |

OTHER PUBLICATIONS

Chem. Abstracts, vol. 51, #13761c (1957).
Chem. Abstracts, vol. 54, #8618i (1960).
Chem. Abstracts, vol. 53, #4112c (1959).
Chem. Abstracts, vol. 53, #4164a (1959).
"176, Eine Methode zur Katalysierten Herstellung von Carbonsaure- und Salfosaure-Chloriden mit Thionylchorid[1])", Bosshard et al., Fasciculus v, vol. XLII (1959), No. 175-176, pp. 1653-1658.
"N-(4-Hydroxyphenyl)Retinamide, A New Retinoid for Prevention of Breast Cancer in the Rat", Moon et al., Cancer Research 39, Apr. (1979), pp. 1339-1346.
"Synthesis and Properties of Some 13-cis- and All-Trans-Retinamides", Shealy et al., J. of Pharm. Sci., vol. 73, No. 6, Jun. (1984), pp. 745-751.
"A Novel Peptide Synthesis", Zaoral and Arnold, Tetrahedron Letters, No. 14 (1960), pp. 9-12.

*Primary Examiner*—Paul J. Killos
*Attorney, Agent, or Firm*—David J. Levy; Leonard R. Hecker

[57] ABSTRACT

A process to prepare retinoyl chlorides, e.g., of the following formula (I):

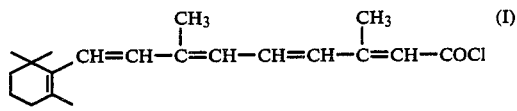

under very mild chlorinating conditions by the action of a reagent amount of dimethylchloroformamidinium chloride on a corresponding retinoic acid.

16 Claims, No Drawings

PROCESS FOR PREPARING RETINOYL CHLORIDES

This invention provides a particularly mild process to prepare retinoyl chlorides in high yields and purity which are suitable for direct conversion to retinoic acid derivatives.

BACKGROUND OF THE INVENTION

Retinoic acid derivatives are known to have useful pharmacologic and other properties. For example, certain ester and amide derivatives of all-trans retinoic acid are disclosed in U.S. Pat. Nos. 4,190,594 and 4,108,880 as having useful ultraviolet (U.V.) absorption properties. In U.S. Pat. No. 4,055,659, the use of esters and amides of all-trans retinoic acid in the treatment of acne is disclosed. N-(4-hydroxyphenyl)-all-trans-retinamide is disclosed in U.S. Pat. No. 4,323,581 as being useful in the prevention of breast cancer in mammals.

Retinoic acid has been previously reported as the starting material in retinoid synthesis. Common to many synthetic routes in the preparation of retinoids is the conversion of retionic acid to retinoyl chloride by the action of various chlorinating reagents such as thionyl chloride or phosphorus trichloride. A common problem associated with the use of these reagents is the instability of retinoyl chloride and retinoic acid to the chlorinating reagent during the conversion of acid, particularly on a large-scale synthesis. For example, R. C. Moon, et al. have reported in Cancer Research, Vol. 39, page 1339 (1979) that the preparation of retinoyl chloride from retinoic acid by the action of phosphorus trichloride in benzene at room temperature for several hours requires the decantation of the benzene-retinoyl chloride solution from a polymeric by-product. In the Moon procedure, the polymeric by-product is formed, probably as a result of the sensitivity of retionic acid which undergoes facile polymerization. In a similar process reported by Y. F. Shealy et al. in the Journal of Pharmaceutical Sciences, Vol. 73, p. 745 (1984), the product retinoyl chloride must be decanted away from a gummy precipitate which the authors report to be "phosphorus compounds". In either case, the yields of retinoids is diminished as a result of poor yield and quality of retinoyl chloride intermediates. In view of the high cost of the starting material, i.e., retinoic acid, such processes may be disadvantageous. In addition, solutions of retinoyl chloride are prone to rapid light, oxygen, heat, and base-catalyzed decomposition.

In a publication by M. Zaorul and Z. Arnold in Tetrahedron Letters No. 14, pages 9–12 (1960) the authors describe the use of dimethylchloroformamidinium chloride as a reagent in the preparation of certain peptides. H. H. Bosshard, et al. have reported in Helv. Chim. Acta. Vol. 42, page 1653 (1959) the conversion of various carboxylic acids to acid chlorides by the action of a catalytic amount of DMF in the presence of thionyl chloride (which led presumably to the catalyst dimethylchloroformamidinium chloride). However, when the Bosshard conditions are applied to the conversion of all-trans retinoic acid to all-trans retinoyl chloride, decomposition of the retinoic acid is rapid which results in lower yields and impure products.

SUMMARY OF THE INVENTION

It has now been discovered that when dimethylchloroformamidinium chloride (III) is used in a reagent capacity with a retinoic acid of the following formula (II), the corresponding retinoyl chloride of the following formula (I) is generated directly under mild conditions in high yield and high purity, according to the following reaction scheme:

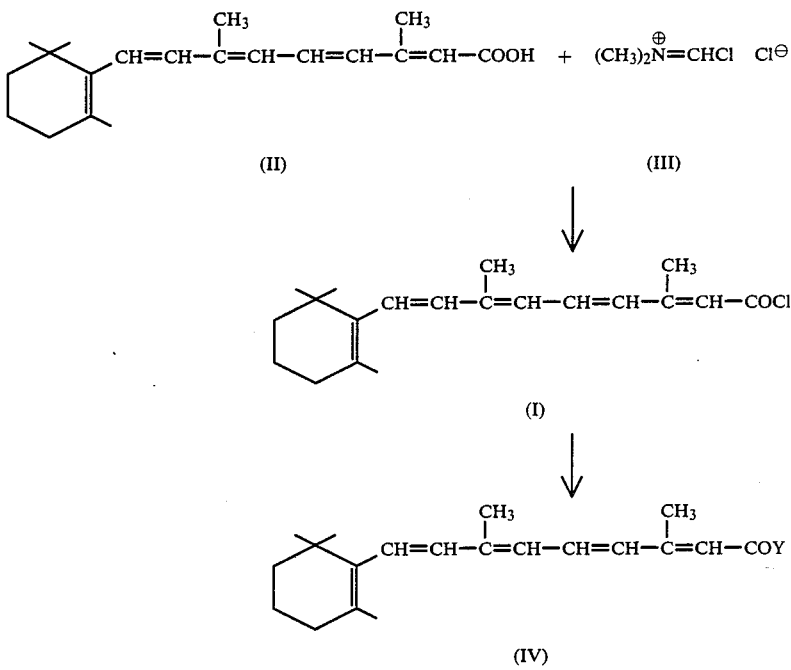

The retinoyl chloride (I) may then be reacted with an active hydrogen compound of the formula HY, where Y is as defined herein, to produce a retinoic acid derivative of the formula (IV). An important aspect of the process of the invention is to form a retinoyl chloride from a retinoic acid in a short reaction time in high yield and high purity under mild chlorination conditions.

DETAILED DESCRIPTION OF THE INVENTION

In the process of this invention, a retinoyl chloride of formula (I) is prepared by chlorinating the analogous retinoic acid of formula (II):

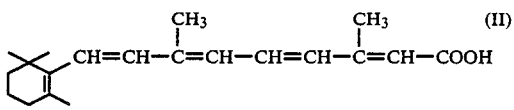

by the action of dimethylchloroformamidinium chloride (III)

in an inert organic solvent. Preferably, in view of the sensitivity of solutions of retinoyl derivatives, especially retinoyl chlorides to heat, light, oxygen, base, solvent, reaction time, and chlorinating agents carefully controlled reaction conditions are maintained during the synthesis and isolation of retinoyl chlorides to avoid rapid and extensive decomposition or polymerization. High yields and purities of retinoyl chlorides are obtained according to the invention by the use of a reagent amount of dimethylchloroformamidinium chloride as the chlorinating agent.

The product retinoyl chlorides of Formula (I) may subsequently be reacted with an active hydrogen compound if the formula HY where Y represents the remaining atoms required to define an amine or alcohol by methods known in the literature or readily apparent to those skilled in the art of organic chemistry. The product is the corresponding retinoic acid derivative, e.g., an amide or ester of Formula (IV) wherein Y represents the remaining atoms required to define said amide or ester. Examples include, but are not limited to, N-(4-hydroxyphenyl)-all-trans-retinamide, N-(4-hydroxyphenyl)-13-cis-retinamide, N-(4-hydroxyphenyl)-7-cis-retinamide, N-(4-hydroxyphenyl)-11-cis-retinamide, N-(4-methoxyphenyl)-all-trans-retinamide, N-(4-ethoxyphenyl)-all-trans-retinamide, and methyl-all-trans-retinoate.

Because of the possibly of numerous cis/trans isomer combinations resulting from the existence of multiple alkene double bonds in the compounds of Formulae (I), (II) and (IV), the terms retinoic acid, retinoyl chloride, retinoid or retinoic acid derivatives are defined to include all possible cis/trans isomeric combinations. However, specific retinoic acids of formula (II) and corresponding reitnoyl chlorides of formula (I) include the following:
(a) all-trans retinoic acid and all-trans retinoyl chloride;
(b) 13-cis-retinoic acid and 13-cis-retinoyl chloride;
(c) 11-cis-retinoic acid and 11-cis-retinoyl chloride;
(d) 7-cis-retinoic acid and 7-cis-retinoyl chloride.

In more detail, the various parameters for the reaction of an acid of formula (II) with dimethylchloroformamidinium chloride (III)

SOLVENT

The reaction solvent is an inert organic solvent in which the starting retinoic acid is at least partially soluble, and which is unreactive to the retinoyl chloride product. Preferably the solvent is a dipolar aprotic solvent and is not an alcohol or primary or secondary amine. Examples of solvents include: ethers, e.g. diethylether, tetrahydrofuran and dioxane; amides, e.g. N,N-dimethylformamide; aromatic hydrocarbons, e.g. benzene and toluene; esters, e.g. ethyl acetate; halocarbons, e.g. methylene chloride; nitriles, e.g. acetonitrile; sulfoxides, e.g. dimethylsulfoxide and sulfolane; and aliphatic hydrocarbons, e.g. hexane. The preferred solvent is N,N-dimethylformamide. In general, to obtain the maximum yield and purity of product, the solvent chosen should be free of water and degassed.

REACTION TIME

In general, the susceptibility of retinoyl chlorides and solutions thereof to polymerization and by-product formation requires that reaction times be minimized in order to obtain high yields and pure products. The process of this invention provides reaction times of up to about two hours, with about 30 minutes to 1½ hours being favored and about 45 minutes to 1 hour preferred. Reaction times at room temperature beyond two hours are undesirable due to polymerization and degradation.

TEMPERATURE

To avoid polymerization and degradation of the product retinoyl chlorides as well as the starting retinoic acids, it is preferred in this process to maintain a reaction temperature below about 50° C., e.g. about 0° C. to about 40° C., with about 20° C. to about 25° C. being most preferred.

EXCLUSION OF OXYGEN

In view of the sensitivity of solutions of retinoyl chlorides to polymerization and degradation by contact with oxygen, it is preferred to operate the reaction under an atmosphere substantially devoid of oxygen. For example, an inert atmosphere of nitrogen or argon can be used to maintain high yields and purities of products.

REDUCED EXPOSURE TO LIGHT

In view of the sensitivity of solutions of retinoyl chloride to daylight or normal room lighting, measures are normally taken to reduce the amount or alter the type of light to which the solutions are exposed. The simplest procedure is is to eliminate substantially all light and conduct the reaction in the dark. However, if light is required, such as during work-up, etc., exposure times and intensity should be minimized or red or yellow light may be used. Alternatively, red or yellow glassware may be used to regulate light exposure.

CHLORINATING AGENT

The chlorinating agent used in the process of the invention is dimethylchloroformamidinium chloride; which may be prepared by the methods of Examples 1 or 3, which are adaptations of the Bosshard et al. procedure. The advantages of using dimethylchloroformamidinium chloride in place of other chlorinating agents are: short reaction time; lower reaction temperature; less by-product formation; and, amenability to large scale synthesis. The quantity of dimethylformamidinium chloride employed must be about stoichiometrically equivalent to the amount of retinoic acid used, i.e., about 0.99 to about 1.10 molar equivalents. Use of lesser amounts may result in poor yields due to incomplete conversion of acid to acid chloride. Conversely, use of greater than 1.10 molar equivalents may result in by-product formation and an impure product which is difficult to purify to obtain a high yield, especially on a large scale.

In order to prepare a retinoyl chloride of formula (I) by the process of this invention, a mixture of the appropriate retinoic acid of formula (II) in an inert organic solvent is treated with about one equivalent of dimethylchloroformamidinium chloride following the conditions detailed above for the various reaction parameters. The resulting product is a solution of the corresponding acid chloride in the reaction solvent which may then be evaporated to yield the desired retinoyl chloride, or, alternatively may be used directly as a stock solution for the preparation of retinoids of formula (IV). Proper handling of such solutions must be maintained in order to minimize the effects of light, heat, oxygen, etc. as detailed above. When reacting a solution of a retinoyl chloride of formula (I) with an active hydrogen substrate of formula YH to produce a retinoic acid derivative of formula (IV), the reaction may be run according to the procedures described in the previously referenced U.S. patents.

In the following Examples and throughout the specification, the following abbreviations may be used: mg (milligrams); g (grams); kg (kilograms); l (liters); ml (milliliters); mmole (millimoles); m (moles); N (normal); mp (melting point); bp (boiling point); E (trans); Z (cis); Et$_2$O (diethyl ether); EtOAc (ethyl acetate); MeOH (methanol); EtOH (ethanol); THF (tetrahydrofuran); DMF (N,N-dimethylforamide); hplc (high pressure liquid chromatography); v/v (volume to volume ratio). Unless otherwise indicated, all temperatures are reported in °C. (degrees centigrade).

EXAMPLE 1

Dimethylchloroformamidinium Chloride (3 Mole Scale)

Dimethylchloroformamidinium chloride was prepared according to the method of H. H. Bosshard, et al. in Helv. Chim. Acta., 42, 1653 (1959). The DMF was stored over 4A sieves and degassed prior to use by bubbling argon through (using a CaSO$_4$ drying trap exit) vigorously for at least one hour. All transfers of all intermediates were done under argon. Dry DMF (224 g, 3.06 m in diethyl ether (6.6 l) in a 12 liter, 3-n round bottom flask was treated with oxalyl chloride (390 g, 3.07 m) as rapidly as evolution of gasses allowed; a colorless precipitate was immediately evident and the reaction was endothermic. After one hour, the solvent was evaporated under vacuum to yield the title compound as a white solid. When removing the flask from the vacuum, argon was bled into the system.

EXAMPLE 2

All-trans-Retinoyl Chloride

Formula (V):

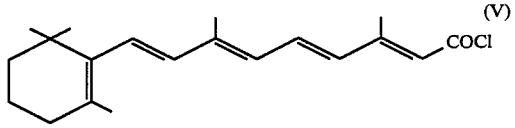

A slurry of retinoic acid (all-trans, 860 g, 2.86 m) in dry DMF (3.5 l) was added to the crude white solid from Example 1, dimethylchloroformamidinium chloride. Care should be taken with retinoic acid since it is a teratogen. After stirring at room temperature for 45 minutes in subdued light (hood lights turned off), the clear deep red retinoyl chloride solution was cooled in ice. This solution is then used in the synthesis of retinoic acid derivatives.

EXAMPLE 3

Dimethylchloroformamidinium Chloride (6 Mole Scale)

A solution of dimethylformamide (448.0 g, 6.28 moles) in anhydrous diethyl ether (12.0 l) was prepared. Oxalic acid chloride (780.0 g, 6.28 moles) was added to the stirred DMF solution at a controlled rate. The vigorous reaction started at ambient temperature. The mixture began to cool because of the rapid evolution of gases (CO, CO$_2$). The rate of addition depends on control of this gas evolution. On this scale, the addition was completed within ca. ½ hour. The solid product began to precipitate at the start of the addition and continued to accumulate during the addition. Stirring was continued for one hour after completion of the addition. It may be necessary to add more ether at this stage to maintain a mobile suspension. The solvent was then evaporated under reduced pressure (10.0 mm) with the external application of steam to the vessel. Argon was added to the vessel to release the vacuum after either removal was complete. Yield of the colorless reagent was quantitative.

EXAMPLE 4

All-trans Retinoyl Chloride

A slurry of all-trans-retinoic acid (1720.0 g, 5.72 moles) in dimethylformamide (7.0 l) was added to dimethylchloroformamidinium chloride (804.0 g, 6.28 moles) with stirring under argon. Intermittent stirring was continued for ¾ to 1 hour after the addition of ambient temperature. The formation of the acid chloride by this method is not a vigorous reaction and may actually be slightly endothermic. However, if the reaction temperature falls below 20° C., the rate of reaction slows. The reaction was monitored by tlc; yield of the acid chloride was assumed to be quantitative if tlc of a sample quenched into ethanol or methanol indicated the absence of retinoic acid; that is to say, only methyl or ethyl ester was noted by tlc. The retinoyl chloride was a clear, deep red solution. If this solution remained at room temperature for more than one hour, it markedly decomposed, became dark, and with time (2–3 hr), a black polymeric material precipitated.

EXAMPLE 5

All-trans-(4-hydroxyphenyl)retinamide (4-HPR)

A solution of all-trans retinoyl chloride (0.20 m) in 350 mL dry, degassed, N,N-dimethylformamide (DMF) prepared according to the procedure of example 4 was added dropwise to a cooled solution of distilled triethylamine (0.40 m, 55.8 mL) and p-aminophenol (87.3 g, 0.8 m) in dry, degassed DMF (200 mL). The temperature was maintained between 10–15 degrees during the addition. The dark colored reaction stirred at room temperature until tlc analysis indicated no remaining acid chloride (about 2 hr.). Water was slowly added until the 4-HPR crystallized. A dark yellow brown solid was collected, washed with water, dried, crystallized from ethanol/water, then toluene/acetone to give 42 g 4-HPR (hplc purity >99%) or 53% yield.

EXAMPLE 6

All-trans-4-(Methoxyphenyl)retinamide a. Into a 500 ml, 3-neck round bottom flask equipped with an overhead stirrer, a thermometer, an addition funnel and a bubbler was placed 5.5 ml (5.24 g, 0.072 m) of dry DMF in about 130 ml of diethyl ether. This was treated with 6.3 ml (9.14 g, 0.72 m) of oxalyl chloride, dropwise, with stirring, over a 20-25 min. period. Gas evolution was very vigorous. A white precipitate was observed about 50 min. after the addition was complete (gas evolution was over) the solvent was removed in vacuo. The white solid (dimethylchloroformamidinium chloride) was placed under argon.

To the white solid was added 21.03 g (0.070 m) of all-trans retinoic acid in about 90 ml of DMF. The mixture became a cloudy orange color, then a clear, dark red. The solution was stirred at room temperature for 35 min., then was cooled in an ice bath. The red retinoyl chloride solution was added dropwise to a solution of 25.8 g (0.21 m) of 4-methoxyaniline in 95 ml of DMF at 10° to 0° C. over a 20 min. period. The dark red solution was cooled in an ice bath for an additional 1½ hours after the addition was complete. Water (50 ml) was added to the solution. Solid began to precipitate immediately. The mixture was filtered and the solid was washed with 200 ml of cold water. The bright yellow solid was dissolved in about 900 ml of hot ethanol. The resulting dark red solution was allowed to cool to room temperature. A precipitate was observed after about one hour. The mixture was filtered. A yellow, fluffy solid was obtained. The material was washed with a small amount of cold ethanol and about 200 ml of water. The solid was dried under vacuum overnight and 16.44 g of a yellow crystalline solid, mp 175°-177° C. was collected. A second crop of product was obtained from the filtrate (6.35 g of a yellow crystalline powder, mp 157°-161° C.).

b. In a similar manner to Example 6a, using 22.5 g (0.075 m) retinoic acid and 27.0 g (0.22 m) of recrystalized p-methoxyaniline a quantitative yield 30.4 g product with mp 178-179 was obtained.

Example 7

13-cis-4-(Hydroxyphenyl)retinamide

Oxalyl chloride (0.1 m, 146 mg) was added at 0 degrees to 6.0 mL dry, degassed DMF. A white precipitate formed. After the slurry stirred for 15 min, a solution of 300 mg 13-cis retinoic acid in 4.0 mL degassed, dry DMF was added. After 20 min., tlc of an adduct quenched in methanol showed that acid chloride formation was nearly complete. The acid chloride solution was added to a solution of 327 mg sublimed 4-aminophenol in 2.0 mL dry degassed DMF. The reaction mixture stirred at 0 degrees protected from light for 2.5 hr. Water (6.7 mL) was added and the reaction stirred until crystals formed; the crystals were collected. Crystallization from methanol, then ethanol/water gave 186 mg, 48% yield of 13-cis-4-(hydroxyphenyl)retinamide.

EXAMPLE 8

All-trans-4-(Ethoxyphenyl)retinamide

A mixture of 5.0 ml of oxalyl chloride and 125 ml of dry DMF was stirred under an atmosphere of argon for 60 hours. To the resulting suspension of dimethylchloroformamidinium chloride was added 15.0 g of all-trans retinoic acid while stirring at room temperature. The resulting clear red-orange solution was cooled to 0° C. and treated with 20.5 g of 4-ethoxyaniline, added dropwise. Yellow solid started to crystallize almost immediately. When the addition was complete, 50 ml of water was added and the yellow solid collected by filtration. Recrystallization twice from ethanol yielded 18.53 g (88.9%) of the title compound, a yellow solid, mp 188°-189° C.

What is claimed is:

1. A process for preparing a retinoyl chloride of formula (I):

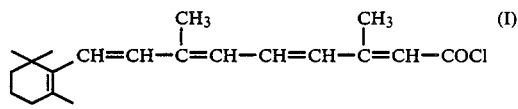

comprising the steps of:
(a) reacting in an inert organic solvent a mixture of a retinoic acid of formula (II):

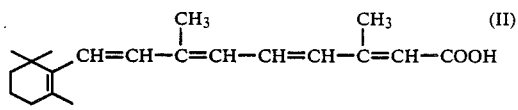

and at least about a stoichiometric amount of dimethylchloroformamidinium chloride previously isolated as a solid, and
(b) optionally isolating the retinoyl chloride from the inert organic solvent.

2. The process of claim 1, wherein said inert organic solvent is a dipolar aprotic solvent.

3. The process of claim 1, wherein said inert organic solvent is selected from the group consisting of an ether, an amide, an aromatic hydrocarbon, an ester, a halocarbon, a nitrile, a sulfoxide, or an aliphatic hydrocarbon.

4. The process of claim 3, wherein said inert organic solvent is diethyl ether, N,N-dimethylformamide, toluene or methylene chloride.

5. The process of claim 4, wherein the inert organic solvent is N,N-dimethylformamide.

6. The process of claim 1, wherein the reaction is maintained at a temperature less than about 50° C.

7. The process of claim 5, wherein the reaction is maintained at a temperature of about 0° C. to less than 50° C.

8. The process of claim 1, wherein the reaction temperature is maintained between about 20° C. and about 25° C.

9. The process of claim 1, wherein the reaction time is of about 30 minutes to about 1½ hours.

10. The process of claim 8, wherein the reaction time is 45 minutes to 1 hour.

11. The process of claim 1, wherein the reaction is carried out under an inert atmosphere.

12. The process of claim 1, wherein the reaction is carried out under an atmosphere of nitrogen or argon.

13. The process of claim 1, wherein the reaction is carried out in the substantial absence of light.

14. The process of claim 1, wherein the retinoic acid is selected from the group consisting of all-trans retinoic acid, 13-cis retinoic acid, 11-cis retinoic acid, and 7-cis retinoic acid.

15. The process of claim 1, wherein said retinoyl chloride is all-trans retinoyl chloride of the following formula (V):

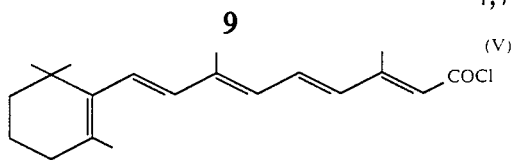
(V)
16. The process of claim 1, wherein said reaction mixture consists essentially of said retinoic acid of formula (II), dimethylchloroformamidinium chloride and said inert organic solvent.
* * * * *